United States Patent [19]

Bugaut et al.

[11] Patent Number: 4,494,953
[45] Date of Patent: Jan. 22, 1985

[54] 2,4-DIHYDROXYDIPHENYLAMINES AND HAIR DYEING COMPOSITIONS AND METHOD

[75] Inventors: Andreé Bugaut, Boulogne; Francoise Estradier, Paris, both of France

[73] Assignee: L'Oreal, Paris, France

[21] Appl. No.: 225,355

[22] Filed: Jan. 15, 1981

Related U.S. Application Data

[62] Division of Ser. No. 27,064, Apr. 4, 1979, Pat. No. 4,263,213.

[30] Foreign Application Priority Data

Apr. 6, 1978 [FR] France .................... 78 10209

[51] Int. Cl.³ .................... A61K 7/13; C09B 57/00
[52] U.S. Cl. .................... 8/408; 8/409; 8/416; 8/421; 8/423; 544/166; 546/232
[58] Field of Search .................... 544/166; 546/232; 8/408, 409, 416, 421, 423

[56] References Cited

U.S. PATENT DOCUMENTS

| | | | |
|---|---|---|---|
| 3,892,749 | 7/1975 | Kalopissis et al. | 546/232 |
| 3,929,404 | 12/1975 | Kalopissis et al. | 546/232 |
| 3,984,443 | 10/1976 | Kalopissis et al. | 8/416 |
| 4,008,999 | 2/1977 | Kalopissis et al. | 8/408 |
| 4,263,213 | 4/1981 | Bugaut et al. | 546/232 |

Primary Examiner—Robert W. Ramsuer
Attorney, Agent, or Firm—Cushman, Darby & Cushman

[57] ABSTRACT

This invention pertains to compounds suitable for dyeing keratin fibers, especially human hair. The compounds have the formula:

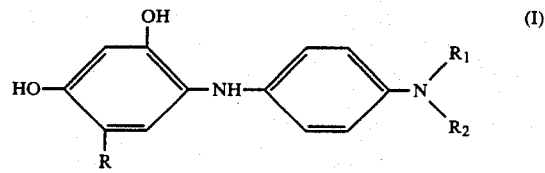

or an acid addition salt thereof, in which formula $R_1$ and $R_2$ form, together with the nitrogen atom to which they are bonded, a morpholino or piperidino ring and R represents a hydrogen atom.

This invention also pertains to compositions for dyeing keratin fibers, especially human hair, such composition containing the compounds set forth above and/or compounds of formula (I) wherein $R_1$ represents a hydrogen atom, $R_2$ represents a tetrahydrofurfuryl or methoxyethyl radical and R represents a hydrogen atom or a methyl radical, or an acid addition salt thereof.

The invention also pertains to the method of using these compositions.

40 Claims, No Drawings

2,4-DIHYDROXYDIPHENYLAMINES AND HAIR DYEING COMPOSITIONS AND METHOD

RELATED APPLICATION

This application is a division of Ser. No. 27,064 filed Apr. 4, 1979, now U.S. Pat. No. 4,263,213.

DESCRIPTION

We have discovered that certain 2,4-dihydroxydiphenylamines can be used as dyestuff precursors in the oxidative dyeing of keratin fibers and especially of human hair. The compounds have the formula:

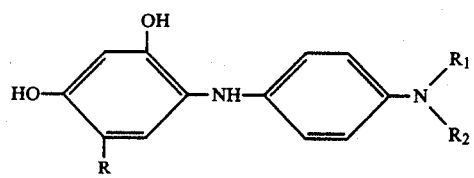

and also their acid salts, in which formula either the substituents $R_1$ and $R_2$ form, together with the nitrogen atom to which they are bonded, a morpholino or piperidino ring and R represents a hydrogen atom, or $R_1$ represents a hydrogen atom, $R_2$ is a tetrahydrofurfuryl or methoxyethyl radical and R represents a hydrogen atom or a methyl radical.

The present invention also provides a composition suitable for dyeing keratin fibres, and especially human hair, which comprises, in solution, at least one 2,4-dihydroxydiphenylamine of the formula (I).

The dyeing compositions according to the invention can also contain at least one other diphenylamine and, in particular, at least one diphenyl of the formula:

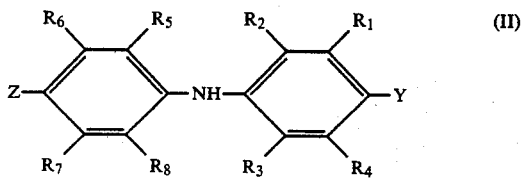

or an acid salt thereof, in which formula: $R_1$ and $R_4$, which are identical or different, each represent a hydrogen or halogen atom or a lower (i.e. of 1 to 6 carbon atoms) alkyl, lower alkoxy, acylamino or ureido group, $R_2$ and $R_3$, which are identical or different, each represent a hydrogen or halogen atom or a lower alkyl, lower alkoxy, amino, N-alkylamino, N-hydroxyalkylamino, acylamino, N-carbamylalkylamino or ureido group, $R_5$ represents a hydrogen or halogen atom or a lower alkyl or lower alkoxy group, $R_6$, $R_7$ and $R_8$, which are identical or different, each represent a hydrogen or halogen atom or a lower alkyl or lower alkoxy group, Y represents a hydroxyl or amino group and Z represents a hydroxyl group or a group of the formula

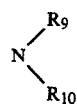

in which $R_9$ and $R_{10}$, which are identical or different, each represent a hydrogen atom or a lower alkyl group which is unsubstituted or substituted by carbamyl, amino, di(lower alkyl) amino, acylamino, lower alkylsulphonamido, arylsulphonamido, sulpho, piperidino, or morpholino or hydroxyalkyl group of 2 to 6 carbon atoms.

The dyeing compositions according to the invention can also contain at least one direct dyestuff and preferably a nitrobenzene dyestuff, such as 3-nitro-4-aminophenol, 3-nitro-4-N-(β-hydroxyethyl)-aminophenol, 3-nitro-6-N-(β-hydroxyethyl)-aminophenol and 3-nitro-4-N'-methylamino-N,N-(β-hydroxyethyl)-aniline.

The dyeing compositions according to the invention can also contain at least one dyestuff of the hydroxynaphthoquinone type, such as 2-hydroxy-1,4-naphthoquinone or 5-hydroxy-1,4-naphthoquinone.

The compositions according to the invention can be used as conventional dye compositions for keratin fibres and especially human hair. The compositions according to the invention can, however, also be used as wavesetting lotions for human hair.

When the compositions according to the invention are used as conventional oxidative dye compositions the said compositions can contain, in addition to the compound (or compounds) of the formula (I) at least one of the following:

(1) para-phenylenediamines and, in particular, para-phenylenediamines of the formula:

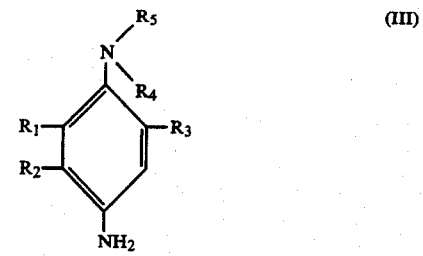

or the corresponding acid salts, in which formula $R_1$, $R_2$ and $R_3$ are identical or different and represent a hydrogen atom, an alkyl radical having from 1 to 4 carbon atoms or an alkoxy radical having 1 or 2 carbon atoms, and $R_4$ and $R_5$ are identical or different and represent a hydrogen atom, an alkyl or hydroxyalkyl radical, an alkoxyalkyl radical in which the alkoxy group contains 1 or 2 carbon atoms, or a carbamylalkyl, mesylaminoalkyl, acetylaminoalkyl, ureidoalkyl or carbethoxyaminoalkyl radical, the alkyl groups in $R_4$ and $R_5$ having from 1 to 4 carbon atoms, with the proviso that $R_1$ and $R_3$ represent hydrogen if $R_4$ and $R_5$ do not both represent a hydrogen atom;

(2) para-aminophenols and, in particular, those which correspond to the formula:

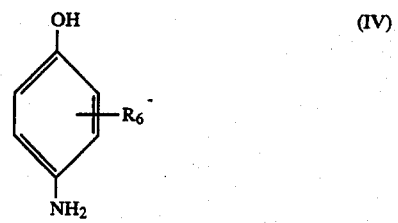

or the corresponding acid salts, in which formula $R_6$ represents a hydrogen atom, an alkyl radical containing from 1 to 4 carbon atoms, or a halogen atom such as chlorine or bromine;

(3) couplers and, in particular, meta-phenylenediamines the disclosure of which is hereby incorporated by such as those described in U.S. Pat. No. 4,125,367, reference, resorcinol, meta-aminophenol, 2-methyl-5-aminophenol, 2-methyl-5-N-(β-hydroxyethyl)-aminophenol, 6-hydroxybenzomorpholine, 2,6-dimethyl-5-acetylaminophenol, 2-methyl-5-carbethoxyaminophenol, 2-methoxy-5-carbethoxyaminophenol and 2-methyl-5-ureidophenol;

(4) ortho-phenylenediamines and ortho-aminophenols optionally containing nuclear substituents and/or substituents on the amine groups, it being possible for these products, by means of complex oxidation mechanisms, to lead to new colored compounds, either by cyclization with themselves or by reaction with para-phenylenediamines;

(5) oxidative dyestuff precursors having benzene structures, which contain at least three groups which are OH, OCH$_3$ or substituted or unsubstituted amino groups, such as 2,6-diamino-4-N,N-diethylaminophenol (for example in the form of the trihydrochloride), 2,5-diamino-4-methylphenol and trihydroxybenzene; and (6) customary adjuvants such as penetrating agents, foaming agents, thickeners, antioxidants, alkalizing agents, perfumes, sequestering agents and film-forming products.

The pH of the dyeing compositions according to the invention should be a basic pH, for example from 8 to 11.5. Among the alkalizing agents which can be used to provide this, there may be mentioned ammonia, alkylamines, such as ethylamine or triethylamine, alkanolamines, such as mono-, di- or triethanolamine, alkylalkanolamines, such as methyldiethanolamine, sodium hydroxide or potassium hydroxide and sodium carbonate, potassium carbonate or ammonium carbonate.

Anionic, cationic, non-ionic or amphoteric water-soluble surface-active agents can also be included in the compositions according to the invention. Among the surface-active agents which can be used in particular, there may be mentioned alkylbenzenesulphonates, alkylnaphthalenesulphonates, sulphates, ether-sulphates and sulphonates of fatty alcohols, quaternary ammonium salts, such as trimethylcetylammonium bromide and cetylpyridinium bromide, diethanolamides of fatty acids, polyoxyethyleneated acids and alcohols and polyoxyethyleneated alkylphenols. The surface-active products are preferably present in the compositions according to the invention in an amount from 0.5 to 30% by weight and advantageously from 4 to 25% by weight.

Organic solvents can also be added to the compositions according to the invention in order to solubilize compounds which are not otherwise sufficiently soluble in water. Among the solvents which can advantageously be used, there may be mentioned, by way of example, ethanol, isopropanol, glycerol, glycols, such as butylglycol, ethylene glycol and propylene glycol, and diethylene glycol monoethyl ether and monomethyl ether. The solvents are advantageously present in the compositions in an amount from 1 to 40% by weight and preferably from 5 to 30% by weight.

Suitable thickeners which can be included in compositions according to the invention include sodium alginate, gum arabic, cellulose derivatives, such as methylcellulose, hydroxyethylcellulose, hydroxypropylmethylcellulose and the sodium salt of carboxymethylcellulose, and acrylic acid polymers as well as inorganic thickeners such as bentonite. The thickeners are preferably present in an amount from 0.5 to 5% by weight, and advantageously from 0.5 to 3% by weight, relative to the total composition.

The antioxidants which can be included in the compositions according to the invention may be, for example, sodium sulphite, thioglycolic acid, sodium bisulphite, ascorbic acid and hydroquinone. These antioxidants can be present in the compositions in an amount of, say, 0.05 to 1.5% by weight, relative to the total weight of the composition.

In general, the compounds of the formula (I) are present in the dyeing compositions according to the invention in an amount from 0.001% to 5% by weight, relative to the total weight of the composition.

The dyeing compositions according to the invention can be in the form of, for example, a liquid, a cream, a gel or an aerosol or in any other form which is suitable for dyeing keratin fibres.

The dyeing compositions in which the diphenylamines of the formula (I) are present can be applied as conventional oxidative dyes with or without the addition of an oxidizing agent, for example hydrogen peroxide, prior to application. As with similar compositions, the compositions according to the invention are suitably kept in contact with the hair for 5 to 30 minutes, after which the treated hair is rinsed and shampooed.

When the compositions according to the invention are used as wavesetting lotions, they are generally applied to hair which has been washed beforehand and the hair is then set in waves and dried with hot air. Wavesetting lotions are usually aqueous-alcoholic solutions containing at least one cosmetic resin and the lotions of this invention are generally in this form. Suitable cosmetic resins include polyvinylpyrrolidone resins, crotonic acid/vinyl acetate copolymers, vinylpyrrolidone/vinyl acetate copolymers and maleic anhydride/butyl vinyl ether copolymers which have been semi-esterified with an alcohol such as methanol, ethanol or butanol. The cosmetic resin is usually employed in an amount from 1 to 3% by weight.

The alcohols which can be used for producing the wavesetting lotions according to this invention are, in particular, low molecular weight alcohols and preferably ethanol or isopropanol; these alcohols are generally used in an amount from 20 to 70% by weight.

The diphenylamines of the formula (I) can be prepared by an anaerobic reaction, with 1,2,4-trihydroxybenzene or trihydroxytoluene, of a para-phenylenediamine in which one of the amine groups is primary and in which the other amine group is secondary or tertiary. The desired diphenylamines can be isolated from the reaction medium for use in the dyeing compositions according to the invention, but it is also possible to use the reaction medium directly, after sufficient reaction time has elapsed, without isolation of the diphenylamines of formula (I). This reaction medium can then be used in conventional oxidative dyeing, with or without the prior addition of hydrogen peroxide.

The following Examples further illustrate the present invention.

EXAMPLE 1

Preparation of 2,4-dihydroxy-4'-N-(β-methoxyethylamino)-diphenylamine dihydrochloride

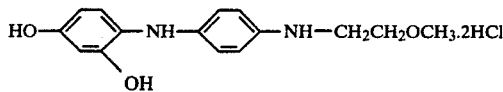

The following solution is prepared:

| | |
|---|---|
| Trihydroxybenzene (1,2,4) | 18.9 g |
| 4-N—(β-Methoxyethylamino)-aniline dihydrochloride | 35.85 g |
| Sodium sulphite | 7.5 g |
| Sodium carbonate | 33 g |
| Water q.s.p. | 750 g |

This solution is kept under nitrogen for one month at 40° C. The oily product which has deposited at the bottom of the reaction medium is separated off by decantation, it is washed with a dilute aqueous solution of sodium sulphite, and hydrochloric acid (d=1.18) is then added thereto. The expected product precipitates in the form of the crystalline dihydrochloride. After recrystallization with the aid of 5N hydrochloric acid solution, the product is filtered off and dried in vacuo. It melts at 180° C. with decomposition.

Elementary analysis of the product obtained gives the following results:

| ANALYSIS | CALCULATED FOR $C_{15}H_{20}N_2O_3Cl$ | FOUND |
|---|---|---|
| C % | 51.87 | 51.65 |
| H % | 5.80 | 5.97 |
| N % | 8.07 | 8.20 |
| Cl % | 20.42 | 19.93–20.07 |

EXAMPLE 2

Preparation of 2,4-dihydroxy-5-methyl-4'-N-(β-methoxyethylamino)-diphenylamine dihydrochloride

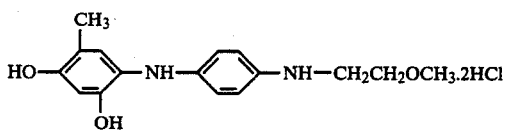

The following solution is prepared:

| | |
|---|---|
| Trihydroxytoluene (1,2,4) | 7 g |
| 4-N—(β-Methoxyethylamino)-aniline dihydrochloride | 11.95 g |
| Sodium sulphite | 2.5 g |
| Sodium carbonate | 11 g |
| Water q.s.p. | 250 g |

This solution is kept in the absence of air for one month at 40° C. The oily product which has deposited at the bottom of the reaction medium is separated off by decantation, it is washed with a dilute solution of sodium sulphite, and hydrochloric acid (d=1.18) is then added thereto. The expected dihydrochloride precipitates in crystalline form. It is filtered off and then recrystallized from 60 ml of 4N hydrochloric acid. After drying in vacuo, the product melts at about 194° C. with decomposition.

Elementary analysis of the product obtained gives the following results:

| ANALYSIS | CALCULATED FOR $C_{16}H_{22}N_2O_3Cl_2$ | FOUND |
|---|---|---|
| C % | 53.19 | 53.17 |
| H % | 6.14 | 6.28 |
| N % | 7.75 | 7.60 |
| Cl % | 19.62 | 19.83 |

EXAMPLE 3

Preparation of 2,4-dihydroxy-4'-tetrahydrofurfurylaminodiphenylamine dihydrochloride

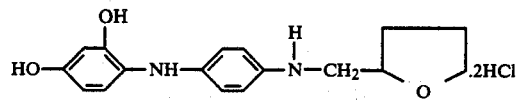

The following solution is prepared:

| | |
|---|---|
| Trihydroxybenzene | 7.5 g |
| 4'-N—Furfurylaminoaniline dihydrochloride | 5.3 g |
| Sodium sulphite | 1.5 g |
| Sodium carbonate | 4.5 g |
| Water q.s.p. | 100 g |

The solution (pH=7.4) is stirred for 20 days under nitrogen at ambient temperature. The oily product which has deposited at the bottom of the reaction medium is separated off by decantation, it is washed with a dilute aqueous solution of sodium sulphite, and 45 ml of absolute ethanol, which has been saturated with hydrogen chloride and diluted with the same volume of a solution of sulphuric acid in either, are then added thereto. The expected diphenylamine precipitates in the form of the crystalline dihydrochloride which melts at about 190° C. with decomposition

EXAMPLE 4

Preparation of 2,4-dihydroxy-5-methyl-4'-tetrahydrofurfurylaminodiphenylamine dihydrochloride

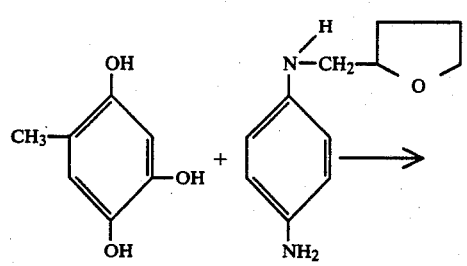

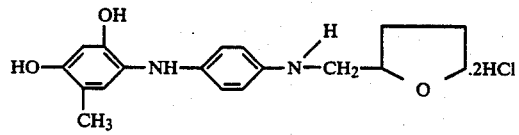

6.16 g (0.04 mol) of 4-amino-N-tetrahydrofurfurylaniline dihydrochloride are dissolved in 200 ml of boiled water containing 8 g of sodium carbonate and 2 g of sodium sulphite. The solution is kept in the absence of air for 8 days at 40° C. The expected product has precipitated in the form of a gummy product. The supernatant liquid is decanted and 8 ml of hydrochloric acid (d=1.19) are added immediately. The expected dihydrochloride crystallizes immediately. The product is filtered off and then recrystallized twice from 5N hydrochloric acid. After drying in vacuo, the product melts at about 185° C. with decomposition.

Elementary analysis of the product obtained gives the following results:

| ANALYSIS | CALCULATED FOR $C_{18}H_{22}N_2O_3.2HCl$ | FOUND |
|---|---|---|
| C % | 55.82 | 55.66 |
| H % | 6.25 | 6.04 |
| N % | 7.23 | 7.02 |
| Cl % | 18.31 | 18.17 |

EXAMPLE 5

Preparation of 2,4-dihydroxy-4'-piperidinodiphenylamine

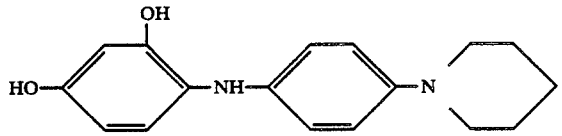

The following solution is prepared:

| Trihydroxybenzene | 9 g |
|---|---|
| N—(4-Aminophenyl)-piperidine dihydrochloride | 14.8 g |
| Sodium sulphite | 4 g |
| Ethanol | 113 g |
| Triethanolamine | 9.6 g |
| Water q.s.p. | 262 g |

This solution (pH=8) is kept in the absence of air for 15 days at 25° C. After 3 days, the expected diphenylamine begins to precipitate in the form of white crystals. After keeping the mixture for 15 days under anaerobic conditions, the crystals are filtered off and washed with a dilute solution of sodium sulphite and then with a small amount of distilled water. After drying in vacuo, the product melts at 176° C.

Elementary analysis of the product obtained gives the following results:

| ANALYSIS | CALCULATED FOR $C_{17}H_{20}N_2O_2$ | FOUND |
|---|---|---|
| C % | 71.80 | 71.53 |
| H % | 7.09 | 7.11 |
| N % | 9.85 | 9.68 |

EXAMPLE 6

Preparation of 2,4-dihydroxy-4'-morpholinodiphenylamine

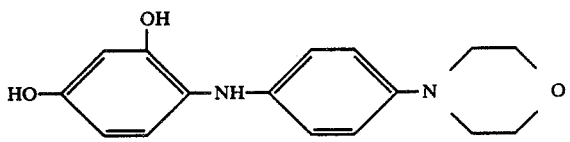

The following solution is prepared:

| Trihydroxybenzene | 0.6 g |
|---|---|
| N—(4-Aminophenyl)-morpholine | 0.85 g |
| Sodium sulphite | 0.03 g |
| Ethanol | 6 g |
| Triethanolamine | 0.1 g |
| Water q.s.p. | 24 g |

This solution (pH=8) is kept in the absence of air for 15 days at 40° C. After 3 days, the expected diphenylamine starts to precipitate in crystalline form. After keeping the mixture for 15 days under anaerobic conditions, the crystals are filtered off, washed with a dilute solution of sodium sulphite and then with a small amount of distilled water and dried in vacuo. After recrystallization from 95° strength ethanol and drying in vacuo, the product melts at 223° C.

Elementary analysis of the product obtained gives the following results:

| ANALYSIS | CALCULATED FOR $C_{16}H_{18}N_2O_3$ | FOUND |
|---|---|---|
| C % | 67.11 | 66.90 |
| H % | 6.34 | 6.47 |
| N % | 9.78 | 9.93 |

EXAMPLE 7

The following dyeing composition is prepared:

| Compound of Example 2 | 1 g |
|---|---|
| Ethanol (96° strength) | 20 g |
| Triethanolamine | 10 g |
| Water q.s.p. | 100 g |

The pH of this composition is equal to 8.5.

When applied to bleached hair for 20 minutes at ambient temperature, this mixture imparts to the hair, after rinsing and shampooing, a light cyclamen coloration.

EXAMPLE 8

The following dyeing composition is prepared:

| Compound of Example 2 | 1 g |
|---|---|
| Ethanol (96° strength) | 20 g |
| Triethanolamine | 10 g |
| Water q.s.p. | 100 g |

The pH of this composition is equal to 8.5.

25 g of hydrogen peroxide of 20 volumes strength are added at the time of use.

When applied to bleached hair for 20 minutes at ambient temperature, this mixture imparts to the hair, after rinsing and shampooing, a princess grey coloration.

EXAMPLE 9

The following dyeing composition is prepared:

| | |
|---|---|
| Compound of Example 1 | 0.8 g |
| Butylglycol | 5 g |
| Oxyethyleneated lauryl alcohol containing 10.5 mols of ethylene oxide (per mol of alcohol) | 5 g |
| Triethanolamine | 6 g |
| Water q.s.p. | 100 g |

The pH of this composition is equal to 8.5.

When applied to naturally white hair for 25 minutes at 25° C., this mixture imparts to the hair, after rinsing and shampooing, a dove grey coloration.

EXAMPLE 10

The following solution is prepared:

| | |
|---|---|
| Compound of Example 1 | 0.2 g |
| Polyvinylpyrrolidone (mean molecular weight = 40,000) sold under the code K 30 by the Company "GENERAL ANILINE AND FILM CORPORATION" | 2 g |
| Isopropanol | 25 g |
| Triethanolamine (in 20% strength aqueous solution) | 2.3 g |
| Water q.s.p. | 100 g |

When applied as a wavesetting lotion to bleached hair, this solution (pH=8) imparts to the hair, after drying with hot air, a beige coloration with a purple pink shade.

EXAMPLE 11

The following solution is prepared:

| | |
|---|---|
| Compound of Example 5 | 0.2 g |
| Vinyl acetate/crotonic acid copolymer (vinyl acetate 90%, crotonic acid 10%) (molecular weight = 45,000 to 50,000) | 2 g |
| Ethanol (96° strength) | 50 g |
| Triethanolamine | 6 g |
| Water q.s.p. | 100 g |

When applied as a wavesetting lotion to bleached hair, this solution (pH=9) imparts to the hair, after drying with hot air, a pearlescent beige coloration with a pinkish sheen.

EXAMPLE 12

The following dyeing composition is prepared:

| | |
|---|---|
| Compound of Example 5 | 1.5 g |
| Butylglycol | 5 g |
| Isopropanol | 20 g |
| Triethanolamine | 5 g |
| Water q.s.p. | 100 g |

The pH of this composition is equal to 9.2.

When applied to bleached hair for 20 minutes at 27° C., this mixture imparts to the hair, after rinsing and shampooing, an ashen beige coloration with a purple-violet shade.

EXAMPLE 13

The following dyeing composition is prepared:

| | |
|---|---|
| Compound of Example 3 | 2 g |
| Sodium lauryl-sulphate containing 19% of starting oxyethyleneated alcohol | 20 g |
| Ethylenediaminetetraacetic acid | 0.1 g |
| Butylglycol | 6 g |
| Sodium bisulphite solution (40% strength) | 1 g |
| Triethanolamine | 4 g |
| Water q.s.p. | 100 g |

The pH of this composition is equal to 8.2.

When applied to 90% naturally white hair for 30 minutes at 25° C., this mixture imparts to the hair, after rinsing and shampooing, a silver grey coloration with a slight violet sheen.

EXAMPLE 14

The following dyeing composition is prepared:

| | |
|---|---|
| Compound of Example 3 | 2 g |
| Sodium lauryl-sulphate containing 19% of starting oxyethyleneated alcohol | 20 g |
| Ethylenediaminetetraacetic acid | 0.1 g |
| Butylglycol | 6 g |
| Sodium bisulphite solution (40% strength) | 1 g |
| Triethanolamine | 4 g |
| Water q.s.p. | 100 g |

The pH of this composition is equal to 8.2.

30 g of hydrogen peroxide of 20 volumes strength are added at the time of use.

When applied to bleached hair for 25 minutes at 25° C., this mixture imparts to the hair, after rinsing and shampooing, a pearlescent, ashen beige coloration.

EXAMPLE 15

The following solution is prepared:

| | |
|---|---|
| Compound of Example 6 | 0.17 g |
| Vinyl acetate/crotonic acid copolymer (vinyl acetate 90%, crotonic acid 10%) (molecular weight = 45,000 to 50,000) | 2 g |
| Ethanol (96° strength) | 50 g |
| Triethanolamine | 2 g |
| Water q.s.p. | 100 g |

The pH of this composition is equal to 8.2.

When applied as a wavesetting lotion to bleached hair, this solution imparts to the hair, after drying with hot air, a golden light blond coloration with a pink sheen.

EXAMPLE 16

The following dyeing composition is prepared:

| | |
|---|---|
| Compound of Example 6 | 1 g |
| Butylglycol | 10 g |
| Ethanol (96° strength) | 6 g |
| Carboxymethylcellulose | 4 g |
| Triethanolamine | 4 g |
| Water q.s.p. | 100 g |

The pH of this composition is equal to 9.4.

When applied to bleached hair for 20 minutes at ambient temperature, this mixture imparts to the hair, after rinsing and shampooing, a pinkish champagne coloration.

EXAMPLE 17

The following dyeing composition is prepared:

| | |
|---|---|
| Compound of Example 4 | 1.16 g |
| Ethanol (96° strength) | 20 g |
| Triethanolamine | 2 g |
| Water q.s.p. | 100 g |

The pH of this composition is equal to 8.

When applied to bleached hair for 30 minutes at 30° C., this mixture imparts to the hair, after rinsing and shampooing, a purple coloration.

EXAMPLE 18

The following dyeing composition is prepared:

| | |
|---|---|
| Compound of Example 2 | 1 g |
| Compound of Example 3 | 0.52 g |
| 4,4'-Dihydroxy-3'-methyl-6'-aminodiphenylamine | 1 g |
| 2,5-Diamino-4-methylphenol dihydrochloride | 0.3 g |
| Butylglycol | 5 g |
| Oxyethyleneated lauryl alcohol containing 10.5 mols of ethylene oxide | 5 g |
| Triethanolamine | 3.5 g |
| Water q.s.p. | 100 g |

The pH of this composition is equal to 7.9

When applied to 90% naturally white hair for 20 minutes at 25° C., this mixture imparts to the hair, after rinsing and shampooing, an ashen light chestnut coloration.

EXAMPLE 19

The following solution is prepared:

| | |
|---|---|
| Compound of Example 3 | 0.5 g |
| Compound of Example 2 | 0.4 g |
| 3-Nitro-4-aminophenol | 0.065 g |
| Vinylpyrrolidone (70%)/vinyl acetate (30%) polymer sold under the code PVP/VA E 735 by the Company "GENERAL ANILINE AND FILM CORPOROATION". | 3 g |
| Ethanol | 25 g |
| Triethanolamine | 1 g |
| Water q.s.p. | 100 g |

The pH of this composition is equal to 7.2.

When applied as a wavesetting lotion to bleached hair, this solution imparts to the hair, after drying with hot air, a copper red coloration.

EXAMPLE 20

The following solution is prepared:

| | |
|---|---|
| Compound of Example 3 | 0.5 g |
| Compound of Example 1 | 0.15 g |
| 4,4'-Dihydroxy-3'-methyl-6'-aminodiphenylamine | 0.3 g |
| Vinylpyrrolidone (60%)/vinyl acetate (40%) copolymer sold under the code PVP/PA S 630 by the Company "GENERAL ANILINE AND FILM CORPORATION" | 2 g |
| Isopropanol | 35 g |
| Triethanolamine | 2.3 g |
| Water q.s.p. | 100 g |

When applied as a wavesetting lotion to bleached hair for 10 minutes at ambient temperature, this solution (pH=8) imparts to the hair, after drying with hot air, a light brown coloration.

EXAMPLE 21

The following dyeing composition is prepared:

| | |
|---|---|
| Compound of Example 2 | 2 g |
| Para-aminophenol | 0.15 g |
| 2-N—(β-Hydroxyethylamino)-4-aminophenoxy-ethanol dihydrochloride | 0.05 g |
| 2-Methyl-5-aminophenol | 0.15 g |
| Oxyethyleneated oleyl alcohol containing 2 mols of ethylene oxide | 5 g |
| Oxyethyleneated oleyl alcohol containing 4 mols of ethylene oxide | 10 g |
| Propylene glycol | 10 g |
| Triethanolamine | 8 g |
| Water q.s.p. | 100 g |

The pH of this composition is equal to 8.4.

20 g of hydrogen peroxide of 20 volumes strength are added at the time of use.

When applied to bleached hair for 20 minutes at 25° C., this mixture imparts to the hair, after rinsing and shampooing, an ashen beige coloration with a pink shade.

EXAMPLE 22

The following solution is prepared:

| | |
|---|---|
| Compound of Example 5 | 0.5 g |
| 4,4'-Dihydroxy-3'-methyl-6'-aminodiphenylamine | 0.5 g |
| 3-Nitro-4-N'—(β-hydroxyethylamino)-N,N—(β-hydroxyethyl)-aniline | 0.15 g |
| Isopropanol | 26 g |
| Quaternary vinylpyrrolidone copolymer sold under the code "GAFquat 734" by the Societe "GENERAL ANILINE FRANCE" in a 50% strength solution in alcohol (mean molecular weight = 100,000) | 1.6 g |
| Ammonia solution (22° B strength) | 0.5 g |
| Water q.s.p. | 100 g |

The pH of this solution is equal to 9.5.

When applied as a wavesetting lotion to bleached hair for 10 minutes at 25° C., this solution imparts to the hair, after drying with hot air, a mahogany coloration.

EXAMPLE 23

The following dyeing composition is prepared:

| | |
|---|---|
| Compound of Example 1 | 1.2 g |
| 4-N,N—(β-Hydroxyethylamino)-3'-methyl-4-hydroxy-6'aminodiphenylamine | 0.7 g |
| 3-Nitro-6-N—(β-hydroxyethylamino)-anisole | 0.05 g |
| 3-Nitro-4-N'—methylamino-N,N—(β-hydroxyethyl)-aniline | 0.8 g |
| Butylglycol | 15 g |
| Diethanolamides of copra fatty acids | 7.5 g |
| Triethanolamine | 8 g |
| Water q.s.p. | 100 g |

The pH of this composition is equal to 8.7.

When applied to naturally white hair for 20 minutes at 25° C., this mixture imparts to the hair, after rinsing and shampooing, a very luminous silvery grey coloration.

EXAMPLE 24

The following dyeing composition is prepared:

| | |
|---|---|
| Compound of Example 1 | 2 g |
| Compound of Example 5 | 0.7 g |
| 2-Hydroxy-1,4-naphthoquinone | 1.5 g |
| Sodium lauryl-sulphate containing 19% of starting oxyethyleneated alcohol | 20 g |
| Ethylenediaminetetraacetic acid | 0.1 g |
| Triethanolamine | 5 g |
| Sodium bisulphite solution (40% strength) | 1 g |
| Water q.s.p. | 100 g |

The pH of this composition is equal to 8.

When applied to bleached hair for 20 minutes at 25° C., this mixture imparts to the hair, after rinsing and shampooing, a coppery chestnut coloration.

EXAMPLE 25

The following dyeing composition is prepared:

| | |
|---|---|
| 4-N—(β-Methoxyethylamino)-aniline dihydrochloride | 3.8 g |
| Trihydroxybenzene | 2 g |
| Ethanol (96° strength) | 20 g |
| Sodium sulphite | 0.1 g |
| Triethanolamine | 11.8 g |
| Water q.s.p. | 100 g |

After keeping this mixture for one month under anaerobic conditions (during which time the product of Example 1 appears in the said mixture), 30 g of hydrogen peroxide of 20 volumes strength are added thereto and it is applied to bleached hair for 25 minutes at ambient temperature. After rinsing and shampooing, an extremely dark purple violet coloration is obtained.

EXAMPLE 26

The following dyeing composition is prepared:

| | |
|---|---|
| 4'-N—Furfurylaminoaniline dihydrochloride | 4.24 g |
| Trihydroxybenzene | 2 g |
| Sodium sulphite | 0.1 g |
| Triethanolamine | 11 g |
| Ethanol | 20 g |
| Water q.s.p. | 100 g |

The pH of this composition is equal to 8.2.

After keeping this mixture for one month under anaerobic conditions (during which time the product of Example 3 appears in the said mixture), 30 g of ethanol are added thereto. The mixture is then applied to 90% naturally white hair for 20 minutes at 25° C. After rinsing and shampooing, a very luminous silver grey coloration with a slight violet shade is obtained.

EXAMPLE 27

If, after keeping the mixture of the preceding Example for one month in the absence of air, initially 30 g of ethanol and then 30 g of hydrogen peroxide of 20 volumes strength are added thereto, and if the dyeing composition is applied to 90% naturally white hair for 20 minutes at 25° C., a dark violet grey coloration is obtained after rinsing and shampooing.

We claim:

1. A 2,4-dihydroxydiphenylamine of the formula:

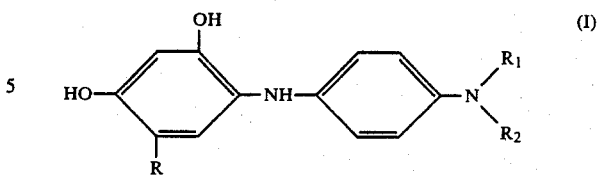

or an acid addition salt thereof, in which formula $R_1$ and $R_2$ form, together with the nitrogen atom to which they are bonded, a morpholino or piperidino ring and R represents a hydrogen atom.

2. A dihydroxydiphenylamine according to claim 1 which is 2,4-dihydroxy-4'-piperidino-diphenylamine.

3. A dihydroxydiphenylamine according to claim 1 which is 2,4-dihydroxy-4'-morpholino diphenylamine.

4. A composition suitable for dyeing keratin fibers which comprises at least one 2,4-dihydroxydiphenylamine of the formula:

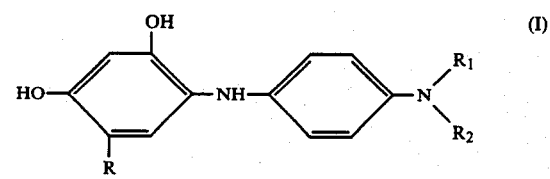

or an acid addition salt thereof, in which formula either $R_1$ and $R_2$ form, together with the nitrogen atom to which they are bonded, a morpholino or piperidino ring and R represents a hydrogen atom, or $R_1$ represents a hydrogen atom, $R_2$ represents a tetrahydrofurfuryl or methoxyethyl radical and R represents a hydrogen atom or a methyl radical, together with an aqueous carrier or diluent.

5. A composition according to claim 4 in which said dihydroxydiphenylamine is 2,4-dihydroxy-4'-N-(β-methoxyethylamino)-diphenylamine dihydrochloride.

6. A composition according to claim 4 in which said dihydroxydiphenylamine is 2,4-dihydroxy-5-methyl-4'-N-(β-methoxyethylamino)-diphenylamine dihydrochloride.

7. A composition according to claim 4 in which said dihydroxydiphenylamine is 2,4-dihydroxy-4'-tetrahydrofurfurylamino-diphenylamine dihydrochloride.

8. A composition according to claim 4 wherein said dihydroxydiphenylamine is 2,4-dihydroxy-5-methyl-4'-tetrahydrofurfurylamino diphenylamine dihydrochloride.

9. A composition according to claim 4 wherein said dihydroxydiphenylamine is 2,4-dihydroxy-4'-piperidino-diphenylamine.

10. A composition according to claim 4 wherein said dihydroxydiphenylamine is 2,4-dihydroxy-4'-morpholino diphenylamine.

11. A composition according to any one of claims 4–10 which contains at least one diphenylamine other than the one encompassed by formula (I).

12. Composition according to claim 11, which contains at least one diphenylamine of the formula:

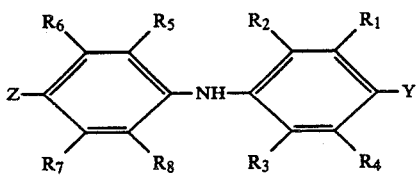

(II)

or an acid addition salt thereof, in which formula: $R_1$ and $R_4$, which are identical or different, each represents a hydrogen or halogen atom or a lower alkyl, lower alkoxy, acylamino or ureido group, $R_2$ and $R_3$, which are identical or different, each represents a hydrogen or halogen atom or a lower alkyl, lower alkoxy, amino, N-alkylamino, N-hydroxyalkylamino, acylamino, N-carbamylalkylamino or ureido group, $R_5$ represents a hydrogen or halogen atom or a lower alkyl or lower alkoxy group, $R_6$, $R_7$ and $R_8$, which are identical or different, each represents a hydrogen or halogen atom or a lower alkyl or lower alkoxy group, Y represents a hydroxyl or amino group and Z represents a hydroxyl group or a group of the formula

in which $R_9$ and $R_{10}$, which are identical or different, each represent a hydrogen atom or a lower alkyl group which is unsubstituted or substituted by carbamyl, amino, di(lower alkyl)amino, acylamino, lower alkylsulphonamido, arylsulphonamido, sulpho, piperidino or morpholino or hydroxyalkyl group of 2 to 6 carbon atoms.

13. Composition according to any one of claims 4–10 which contains at least one direct dyestuff.

14. Composition according to claim 13, in which the direct dyestuff is 3-nitro-4-aminophenol, 3-nitro-4-N-(β-hydroxyethyl)-aminophenol, 3nitro-6-N-(β-hydroxyethyl)-aminophenol, 3-nitro-4-N'-methylamino-N,N-(β-hydroxyethyl)-aniline, 2-hydroxy-1,4-naphthoquinone or 5-hydroxy-1,4-naphthoquinone.

15. A composition for dyeing human hair according to any one of claims 4–10 which contains at least one paraphenylenediamine of the formula:

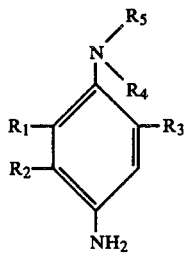

(III)

or an acid addition salt thereof, in which formula $R_1$, $R_2$ and $R_3$ are identical or different and represent a hydrogen atom, an alkyl radical having from 1 to 4 carbon atoms or an alkoxy radical having from 1 or 2 carbon atoms, and $R_4$ and $R_5$ are identical or different and represent a hydrogen atom, an alkyl or hydroxyalkyl radical, an alkoxyalkyl radical in which the alkoxy group contains from 1 or 2 carbon atoms, or a carbamylalkyl, mesylaminoalkyl, acetylaminoalkyl, ureidoalkyl or carbethoxyaminoalkyl radical, the alkyl groups in $R_4$ and $R_5$ having from 1 to 4 carbon atoms, with the provide that $R_1$ and $R_3$ represent hydrogen if $R_4$ and $R_5$ do not represent a hydrogen atom.

16. A composition according to any one of claims 4–10 which contains at least one para-aminophenol corresponding to the formula:

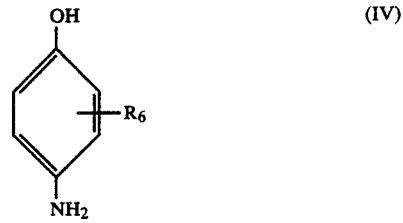

(IV)

or an addition salt thereof, in which formula $R_6$ represents a hydrogen atom, an alkyl radical containing from 1 to 4 carbon atoms, or a halogen atom.

17. Composition according to claims 4–10 which contains at least one coupler.

18. Composition according to claim 17 in which the coupler is a meta-phenylenediamine, resorcinol, meta-aminophenol, 2-methyl-5-aminophenol, 2-methyl-5-N-(β-hydroxyethyl)-aminophenol, 6-hydroxybenzomorpholine, 2,6-dimethyl-5-acetylaminophenol, 2-methyl-5-carbethoxyaminophenol, 2-methoxy-5-carbethoxyaminophenol or 2-methyl-5-ureidophenol.

19. Composition according to any one of claims 4–10 which contains at least one ortho-phenylenediamine or ortho-aminophenol.

20. Composition according to claims 4–10 which contains at least one oxidative dye precursor having the benzene structure, which contains at least three groups which are OH, $OCH_3$ and substituted or unsubstituted amino groups.

21. Composition according to claim 20 in which the oxidative precursor is 2,6-diamino-4-N,N-diethylaminophenol, 2,5-diamino-4-methylphenol, trihydroxybenzene or trihydroxytoluene.

22. Composition according to claims 4–10 which contains at least one of a penetrating agent, foaming agent, thickener, antioxidant, alkalizing agent, perfume, sequestering agent or film-forming product.

23. Composition according to claim 22, in which the alkalizing agent is ammonia, an alkylamine, alkanolamine or alkylalkanolamine, sodium hydroxide or potassium hydroxide or sodium carbonate, potassium carbonate or ammonium carbonate.

24. Composition according to claims 4–10 which has a pH from 8 to 11.5.

25. Composition according to claims 4–10 which contains at least one water-soluble surface-active agent in an amount from 0.5 to 30% by weight, based on the total weight of the composition.

26. Composition according to claim 25 in which the surface-active agent is present in an amount from 4 to 25% by weight based on the total weight of the composition.

27. Composition according to claim 25 in which the surface-active agent is an alkylbenzenesulphonate, alkylnaphthalesesulphonate, sulphate, ether-sulphate or sulphonate of a fatty alcohol, a trimethylcetylammonium bromide or cetylpyridinium bromide, a fatty acid diethanolamide, a polyoxyethyleneated acid or alcohol or a polyoxyethyleneated alkylphenol.

28. Composition according to claims 4-10 which contains at least one organic solvent in an amount from 1 to 40% by weight, based on the total weight of the composition.

29. Composition according to claim 28 in which the organic solvent is present in an amount from 5 to 30% by weight based on the total weight of the composition.

30. Composition according to claim 28 in which the organic solvent is ethanol, isopropanol, glycerol, butylglycol, ethylene glycol, propylene glycol, or diethylene glycol monoethyl ether or monomethyl ether.

31. Composition according to claim 22 which contains at least one thickener in an amount from 0.5 to 5% by weight, based on the total weight of the composition.

32. Composition according to claim 31 in which the thickener is present in an amount from 0.5 to 3% by weight based on the total weight of the composition.

33. Composition according to claim 22 in which the thickener is sodium alginate, gum arabic, a cellulose derivative, an acrylic acid polymer or bentonite.

34. Composition according to claim 22 which contains at least one antioxidant in an amount from 0.05 to 1.5% by weight, based on the total weight of the composition.

35. Composition according to claim 22 in which the antioxidant is sodium sulphite, thioglycolic acid, sodium bisulphite, ascorbic acid or hydroquinone.

36. Composition according to any one of claims 4-10 in which the compound of formula (I) is present in an amount from 0.001% to 5% by weight, based on the total weight of the composition.

37. Composition according to claims 4-10 which is in the form of a liquid, a cream, a gel or an aerosol.

38. Composition according to any one of claims 4-10 in which the diphenylamine of formula (I) is formed in situ.

39. A method of dyeing human hair which comprises applying thereto a composition as defined in any one of claims 4-10.

40. A method according to claim 39 in which hydrogen peroxide is added to said composition before application.

* * * * *